(12) United States Patent
Kuramae

(10) Patent No.: US 11,974,905 B2
(45) Date of Patent: May 7, 2024

(54) ABSORBENT SHEET AND ABSORBENT ARTICLE

(71) Applicant: Kao Corporation, Tokyo (JP)

(72) Inventor: Ryota Kuramae, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 1334 days.

(21) Appl. No.: 16/472,457

(22) PCT Filed: Dec. 7, 2017

(86) PCT No.: PCT/JP2017/043992
§ 371 (c)(1),
(2) Date: Jun. 21, 2019

(87) PCT Pub. No.: WO2018/116849
PCT Pub. Date: Jun. 28, 2018

(65) Prior Publication Data
US 2020/0306108 A1    Oct. 1, 2020

(30) Foreign Application Priority Data

Dec. 22, 2016 (JP) ................................ 2016-250165
Oct. 26, 2017 (JP) ................................ 2017-207303

(51) Int. Cl.
| | | |
|---|---|---|
| *A61F 13/539* | (2006.01) | |
| *A61F 13/53* | (2006.01) | |
| *A61L 15/24* | (2006.01) | |
| *A61L 15/26* | (2006.01) | |
| *A61L 15/30* | (2006.01) | |
| *A61L 15/58* | (2006.01) | |
| *C09J 7/35* | (2018.01) | |

(52) U.S. Cl.
CPC ............ *A61F 13/539* (2013.01); *A61L 15/24* (2013.01); *A61L 15/26* (2013.01); *A61L 15/30* (2013.01); *A61L 15/58* (2013.01); *C09J 7/35* (2018.01); *A61F 2013/530218* (2013.01); *A61F 2013/530226* (2013.01); *C09J 2421/00* (2013.01); *C09J 2433/00* (2013.01); *C09J 2483/00* (2013.01)

(58) Field of Classification Search
CPC ...................................................... A61L 15/16
See application file for complete search history.

(56) References Cited

U.S. PATENT DOCUMENTS

| | | | |
|---|---|---|---|
| 4,721,647 A | 1/1988 | Nakanishi et al. | |
| 5,830,202 A * | 11/1998 | Bogdanski | A61F 13/5323 604/378 |
| 5,962,068 A | 10/1999 | Tsuchiya et al. | |
| 9,072,635 B2 | 7/2015 | Katsuragawa et al. | |
| 9,695,341 B2 * | 7/2017 | Thatcher | C08L 23/22 |
| 2002/0115969 A1 | 8/2002 | Maeda et al. | |
| 2003/0181115 A1 | 9/2003 | Nagasuna et al. | |
| 2009/0264845 A1 | 10/2009 | Himori et al. | |
| 2010/0030177 A1 | 2/2010 | Sanada et al. | |
| 2011/0092943 A1 | 4/2011 | Bishop et al. | |
| 2012/0083756 A1 | 4/2012 | Takahashi et al. | |
| 2013/0338622 A1 | 12/2013 | Bishop et al. | |
| 2015/0202095 A1 | 7/2015 | Kawakami et al. | |
| 2016/0199528 A1 * | 7/2016 | Tönnessen | A61L 15/24 604/372 |

FOREIGN PATENT DOCUMENTS

| | | |
|---|---|---|
| CN | 102427784 A | 4/2012 |
| CN | 104302264 A | 1/2015 |
| CN | 106010381 A | 10/2016 |
| CN | 106137555 A | 11/2016 |
| EP | 1 088 537 A2 | 4/2001 |
| EP | 1 447 067 A1 | 8/2004 |
| EP | 1 649 928 A1 | 4/2006 |
| EP | 2 301 499 A1 | 3/2011 |
| EP | 2 314 264 A1 | 4/2011 |
| EP | 2 383 115 A1 | 11/2011 |
| EP | 2 524 676 A1 | 11/2012 |
| EP | 2 524 679 A1 | 11/2012 |
| JP | 2003-10680 A | 1/2003 |
| JP | 2003-275240 A | 9/2003 |
| JP | 2003-290290 A | 10/2003 |
| JP | 2007-143677 A | 6/2007 |

(Continued)

OTHER PUBLICATIONS

International Search Report (PCT/ISA/210) issued in PCT/JP2017/043992, dated Feb. 20, 2018.
Third Party Observation issued in PCT/JP2017/043992, dated Apr. 18, 2019.
Extended European Search Report for European Application No. 17883085.7, dated Jun. 30, 2020.

*Primary Examiner* — Gina C Justice
(74) *Attorney, Agent, or Firm* — Birch, Stewart, Kolasch & Birch, LLP

(57) ABSTRACT

An absorbent member (20) includes an absorbent sheet (10) in which absorbent polymer (12) is fixed to a base sheet (11) and a cover sheet (21) covering at least a first surface of the absorbent sheet (10). The absorbent sheet (10) has an absorbent polymer fixing proportion of 40% or more. The absorbent member (20) has high fixing performance of the absorbent polymer (12) to the base sheet (11) and is less likely to suffer from detachment of the absorbent polymer (12) even after liquid absorption. The absorbent polymer (12) is preferably fixed to the base sheet (11) with a base sheet fixing adhesive (13) interposed therebetween. The adhesive (13) is preferably an acrylic, silicone-based or rubber-based adhesive, and is preferably a hot-melt adhesive.

13 Claims, 2 Drawing Sheets

(56) References Cited

FOREIGN PATENT DOCUMENTS

| | | |
|---|---|---|
| JP | 2008-183159 A | 8/2008 |
| JP | 2012-152472 A | 8/2012 |
| JP | 2012-217652 A | 11/2012 |
| JP | 2013-10361 A | 1/2013 |
| JP | 2013-255818 A | 12/2013 |
| JP | 2016-209124 A | 12/2016 |
| RU | 2 529 109 C2 | 9/2014 |

\* cited by examiner

ABSORBENT SHEET AND ABSORBENT ARTICLE

TECHNICAL FIELD

The present invention relates to an absorbent sheet for use in absorbing liquid, and more particularly an absorbent sheet preferably for use as an absorbent member of an absorbent product such as a sanitary napkin or a disposable diaper.

BACKGROUND ART

In a known absorbent sheet for use as an absorbent member of an absorbent product, absorbent polymer is fixed to a base sheet. The absorbent sheet having this structure is thin and is not bulky compared to an absorbent member including a laminated fiber body of a fiber member such as pulp fibers, and thus, is mainly used for a thin absorbent product.

Patent Literatures 1 and 2 describe absorbent sheets in which a large amount of absorbent polymer particles are fixed to one surface of a base sheet made of, for example, nonwoven fabric by a hot-melt adhesive. Regarding the hot-melt adhesive for fixing absorbent polymer particles to the base sheet, Patent Literature 1 describes that an acrylic elastomer and a rubber adhesive are preferable because such an adhesive can ensure fixture of absorbent polymer particles swelled after liquid absorption and is easy to extend so as to follow expansion of the absorbent polymer particles by swelling, and Patent Literature 2 further describes a silicone-based hot-melt adhesive.

CITATION LIST

Patent Literatures

Patent Literature 1: US 2002/0115969 A
Patent Literature 2: EP 1447067 A1

SUMMARY OF INVENTION

The present invention provides an absorbent sheet that is an absorbent sheet in which absorbent polymer is fixed to a base sheet, and which has an absorbent polymer fixing proportion of 40% or more.

The present invention also provides an absorbent member including the absorbent sheet according to the present invention described above and a cover sheet covering at least a first surface of the absorbent sheet.

The present invention also provides a method for producing an absorbent sheet that is the absorbent sheet according to the present invention described above in which the absorbent polymer is fixed to the base sheet with a base sheet fixing adhesive interposed therebetween, and the method includes a step of applying an adhesive onto a first surface of the base sheet and then spraying small pieces of absorbent polymer onto the first surface.

DESCRIPTION OF EMBODIMENTS

A conventional absorbent sheet shows low fixing performance of absorbent polymer to a base sheet. Thus, in a case where absorbent polymer is particulate, for example, a considerable amount of absorbent polymer particles has been already detached from the base sheet before use in some cases. In a case where the absorbent sheet is used as an absorbent member of an absorbent product, for example, the absorbent polymer particles are detached from the base sheet in some cases because of swelling of the absorbent polymer particles caused by absorption of body fluid such as urine. Absorbent polymer particles detached from an absorbent sheet in an absorbent product might become clusters and cause an absorbent product user to feel hardness and also provide gritty feeling due to rubbing among the particles. These feelings can cause fit degradation. In addition, since absorption performance degrades in a region of the absorbent sheet where absorbent polymer has been detached, liquid leakage and liquid return might occur.

In view of this, the present invention provides an absorbent sheet and an absorbent member that show high fixing performance of absorbent polymer to a base sheet and are less likely to suffer from detachment of absorbent polymer even after liquid absorption.

Figure 1:
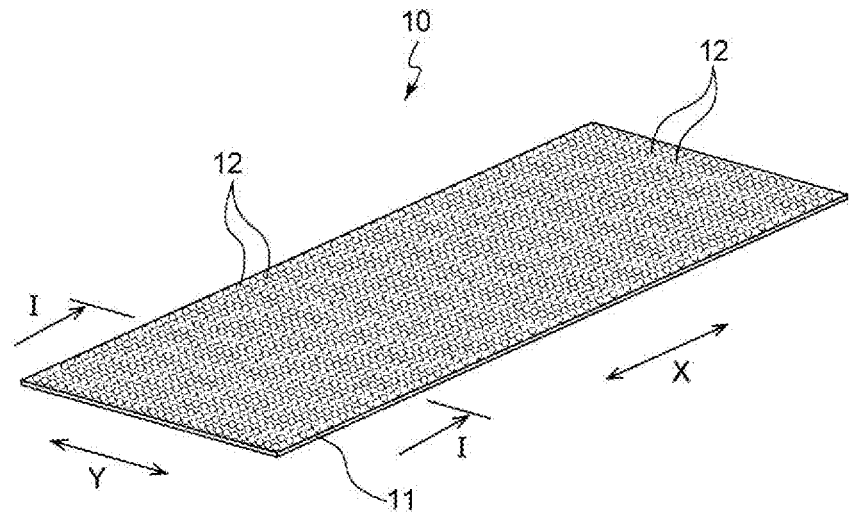
FIG. 1 is a perspective view schematically illustrating one embodiment of an absorbent sheet according to the present invention.
Figure 2:
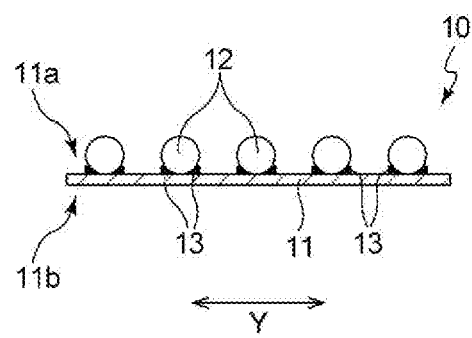
FIG. 2 is a cross-sectional view schematically illustrating a part of a cross section taken along line I-I in FIG. 1.

The present invention will be described hereinafter with reference to the drawings using preferred embodiments. FIGS. 1 and 2 illustrate an absorbent sheet 10 that is one embodiment of an absorbent sheet according to the present invention. The absorbent sheet 10 includes a base sheet 11 including a first surface 11a and a second surface 11b and absorbent polymer 12 fixed to the base sheet 11. The absorbent sheet 10 has a longitudinal direction X and a width direction Y orthogonal to the longitudinal direction X.

In the absorbent sheet 10, the surfaces 11a and 11b of the base sheet 11 are substantially flat (macroscopically). The absorbent polymer 12 is fixed to the flat first surface 11a of the base sheet 11 with an adhesive 13 interposed therebetween, and the absorbent polymer 12 is not fixed to the second surface 11b of the base sheet 11. In the absorbent sheet 10, the first surface 11a of the base sheet 11 to which the absorbent polymer 12 is fixed serves as a liquid absorbing surface. This configuration in which "the absorbent polymer 12 is fixed to the first surface 11a of the base sheet 11 with the adhesive 13 interposed therebetween, and the absorbent polymer 12 is not fixed to the second surface 11b" is preferable because this configuration can promote formation of a gap due to bending of the base sheet 11 after liquid absorption and swelling of the absorbent polymer 12 described later, and can contribute to enhancement of absorption performance.

The base sheet 11 only needs to be a sheet-like material to which the absorbent polymer 12 can be fixed, and may be either liquid permeable or liquid impermeable. Examples of the base sheet 11 include a fiber structure such as a nonwoven fabric, a woven fabric, a knitted fabric, and paper, as well as resin films, foams, and nets. In particular, from the viewpoint of reduction of thickness of the absorbent sheet 10 and enhancement of flexibility of the absorbent sheet 10, the base sheet 11 preferably includes a nonwoven fabric or a resin film. That is, the base sheet 11 is preferably made of one of the nonwoven fabric or the resin film or may be a combined sheet including both the nonwoven fabric and the resin film.

The nonwoven fabric constituting the base sheet 11 may be any fabric formed by various methods without any particular limitation, and may be, for example, an air-through nonwoven fabric, a heat roll nonwoven fabric, a spunlace nonwoven fabric, a spunbond nonwoven fabric, a meltblown nonwoven fabric, or a spunbond-meltblown-spunbond (SMS) nonwoven fabric. These nonwoven fabrics may be hydrophilic nonwoven fabrics made of fibers subjected to a hydrophilic treatment. Among these nonwoven fabrics, the SMS nonwoven fabric is especially effective for reducing the thickness of the absorbent sheet 10 and enhancing flexibility of the absorbent sheet 10, and thus, is preferably used as the base sheet 11.

Examples of materials for the resin film constituting the base sheet 11 include polyurethane resins, polyester resins such as polyethylene terephthalate (PET), polyolefin resins such as polyethylene (PE) and polypropylene (PP), polyamide resins, polyvinyl alcohol, and modified materials and copolymers of these resins. In view of enhancement of liquid permeability, the resin film may have a plurality of holes penetrating the resin film in the thickness direction thereof. Among these resin films, the polyolefin resin especially has high flexibility and high processability, and therefore, is preferably used as the base sheet 11.

In the absorbent sheet 10, the absorbent polymer 12 is particulate, and a large amount of particulate absorbent polymer 12 is fixed to the first surface 11a of the base sheet 11. The particulate absorbent polymer 12 is not limited to a specific shape, and may have a spherical shape, a cluster shape, a barrel shape, or an irregular shape, for example. The particulate absorbent polymer 12 is not limited to a specific average particle size, but from the viewpoint of a balance between fixing performance and absorption performance, the average particle size is preferably 50 μm or more and more preferably 200 μm or more, and preferably 800 μm or less and more preferably 500 μm or less.

In the present invention, the form of the absorbent polymer is not limited to particles, and the absorbent polymer can be in various forms. The present invention has been made in view of a problem that a relatively small contact area between absorbent polymer and a base sheet (i.e., an area of a portion fixed to the base sheet) is likely to cause detachment of the absorbent polymer from the base sheet. Thus, as a form of the absorbent polymer according to the present invention, a form that especially susceptible to such a problem is typically small pieces sufficiently smaller than the base sheet. Such small pieces of the absorbent polymer are not limited to the particulate form and may be a fiber shape, a sheet shape, or a shape obtained by cutting sheet-like absorbent polymer into small predetermined shapes such as strips.

The absorbent polymer 12 may be any material usable in the absorbent sheet of this type without any particular limitation, and may be sodium polyacrylate, (acrylic acid-vinyl alcohol) copolymer, sodium polyacrylate cross-linked polymer, (starch-acrylic acid) graft polymer, (isobutylene-maleic anhydride) copolymer, and a saponified product thereof, potassium polyacrylate, or cesium polyacrylate, for example. These materials may be used alone or two or more of them may be used in combination.

The absorbent polymer 12 preferably has a high water-absorbing property. If the water-absorbing property increases, however, the degree of swelling due to water absorption increases and the absorbent polymer 12 might be detached. In view of this, in a case where a centrifugal retentive capacity is used as an index of water-absorbing property of the absorbent polymer used in the present invention, the centrifugal retentive capacity of the absorbent polymer is preferably 10 g/g or more, more preferably 20 g/g or more, and even more preferably 30 g/g or more, and preferably 60 g/g or less and more preferably 50 g/g or less. The centrifugal retentive capacity (water absorption capacity) of the absorbent polymer is measured by the following method.

Method for Measuring Centrifugal Retentive Capacity of Absorbent Polymer

The centrifugal retentive capacity is measured in conformity with JIS K 7223 (1996). A nylon woven fabric (supplied by Sanriki Seisakusyo Co., Ltd., product name: nylon screen, standard: 250 mesh) is cut into a rectangle having a width of 10 cm and a length of 40 cm. This rectangle is folded into two at a longitudinal center and is heat-sealed at both ends thereof so that a nylon bag having a width of 10 cm (internal dimension of 9 cm) and a length of 20 cm is prepared. Next, 1.00 g of absorbent polymer as a measurement sample is precisely weighted, and is uniformly placed in a bottom portion of the prepared nylon bag. Thereafter, the nylon bag including the sample is immersed in physiological saline (0.9 mass % sodium chloride aqueous solution) controlled to 25° C. After one hour from the start of the immersion, the nylon bag is taken out of the physiological saline, and is suspended vertically for one hour to be drained, and then dried by a centrifugal dryer (manufactured by KOKUSAN Co., Ltd., product type H-130C special model). Drying conditions are at 143 G (800 rpm) and for 10 minutes. After drying, the mass of the sample is measured, and a target centrifugal retentive capacity (water absorption capacity) is calculated by:

$$\text{centrifugal retentive capacity (g/g)} = (a'-b-c)/c$$

wherein a' represents a total mass (g) of the sample after centrifugal drying and the nylon bag, b represents a mass (g) of the nylon bag before water absorption (dried), and c represents a mass (g) of the sample before water absorption (dried).

The measurement is performed five times (n=5), the largest value and the smallest value are removed, and the average of the other three values is used as a measured value. The measurement is performed at 23±2° C., with a humidity of 50±5% and the sample is held in the same environment for 24 hours or more before the measurement.

A main feature of the absorbent sheet 10 is that the absorbent polymer fixing proportion is 40% or more. The absorbent polymer fixing proportion is a percentage of absorbent polymer that is not detached after placement of an absorbent sheet as a measurement target in physiological saline (0.9 mass % saline) being stirred at a predetermined rotational speed, and can be an index of fixing performance of the absorbent polymer that has absorbed liquid and swelled to the base sheet. As the absorbent polymer fixing proportion increases, the fixing performance of absorbent polymer to the base sheet in the absorbent sheet increases, and detachment of absorbent polymer does not easily occur even after liquid absorption, to say nothing of before use. The absorbent polymer fixing proportion is measured by the following processes 1 through 5.

(Process 1) An absorbent sheet having 5 cm-square shape in plan view is prepared as a measurement sample. The measurement sample is temporarily suspended vertically with ends of the measurement sample being held, and then, the weight (initial sample weight) of the measurement sample is measured.

(Process 2) The entire measurement sample is immersed in physiological saline, and after 30 minutes from the start of the immersion, the measurement sample is taken out of the physiological saline.

(Process 3) A cylindrical stirrer having a diameter of 35 mm and an axial length of 12 mm and 300 ml of physiological saline are placed in a beaker having a capacity of 300 ml, and the stirrer is rotated at the number of rotations of 600±5 rpm using a magnetic stirrer, thereby stirring the physiological saline. The measurement sample subjected to process 2 described above is placed in this physiological saline being stirred, and after 30 seconds after the placement, the measured sample is taken out of the physiological saline.

(Process 4) The measurement sample in a wet state subjected to process 3 is allowed to stand for 12 hours in a constant temperature bath whose internal temperature is set at 105° C., and the weight (post-stirring sample weight) of the measurement sample in a dried state is measured.

(Process 5) The total weight of members except absorbent polymer is subtracted from each of the initial sample weight and the post-stirring sample weight, thereby calculating an initial absorbent polymer weight (W0) and a post-stirring absorbent polymer weight (W1). Then, an absorbent polymer fixing proportion of the measurement sample (absorbent sheet) is calculated by:

fixing percentage of absorbent polymer (%)=($W1$/$W0$)×100

In process 1, the reason for temporarily suspending the measurement sample (absorbent sheet having a 5 cm-square shape in plan view) vertically while holding ends of the sample is to remove non-fixed materials such as absorbent polymer disposed on, but not fixed to, the base sheet (e.g., absorbent polymer not fixed with, for example, an adhesive and simply sprayed onto the base sheet from above). In the operation of suspending the measurement sample, the sample only needs to be suspended substantially vertically for about three to five seconds with the ends of the sample being held. The suspended measurement sample does not need to be tapped or shaken significantly. In suspending the measurement sample, an end of the measurement sample is first held with, for example, tweezers and the sample is suspended for three to five seconds. Thereafter, the opposite end of the sample, that is, an end opposite to the end held in the suspension, is held and the sample is then suspended for three to five seconds.

In process 1, in a case where the 5 cm-square absorbent sheet cannot be prepared as a measurement sample (e.g., a case where the size of the measurement sample is less than 5 cm square because of a small size of the absorbent sheet), a plurality of small-size measurement samples each having a size less than 5 cm square are taken from an evaluation target sheet in such a manner that the total of single-side areas of the plurality of measurement samples is 25 cm². Subsequently, an absorbent polymer fixing proportion is measured in accordance with processes 1 through 5 for each of the plurality of measurement samples, and an average value of the thus-obtained absorbent polymer fixing proportions is used as an absorbent polymer fixing proportion of the absorbent sheet.

Examples of measurement equipment used in process 3 include the following equipment.

Magnetic stirrer: HI-304N (manufactured by HANNA, reverse stirrer)

Stirrer: Start Head NALGENE (6600-0035) [35φ×12 mm]

Beaker: 300 ml [78φ×103 mm]

In the absorbent sheet according to the present invention, absorbent polymer only needs to be fixed to the base sheet and have an absorbent polymer fixing proportion of 40% or more. The absorbent polymer may be fixed to the base sheet by any means. The means for fixing is typically an adhesive, and as described above, in the absorbent sheet 10, the absorbent polymer 12 is fixed to the surface (first surface 11a) of the base sheet 11 with the adhesive 13 interposed therebetween. From the viewpoint of obtaining an absorbent polymer fixing proportion of 40% or more, absorbent polymer is preferably fixed to the base sheet with the base sheet fixing adhesive interposed therebetween, and a higher absorbent polymer fixing proportion of 60% or more, and further 80% or more, can be obtained by appropriately selecting type of the adhesive, for example. The adhesive according to the present invention includes both a "strict adhesive that is liquid (in a state having a fluidity) before use and becomes solid when a non-adhesive object is attached to the adhesive" and a "tackiness agent having properties of both liquid and solid and always stably remaining in a wet state."

Examples of a fixing form of absorbent polymer using fixing means except an adhesive include a form in which absorbent polymer is attached directly to a surface of the base sheet without interposition of another member such as an adhesive. This direct attaching form of absorbent polymer can be obtained by performing production (polymerization reaction) of absorbent polymer on the base sheet.

The absorbent sheet according to the present invention includes not only a form in which absorbent polymer is fixed to a surface of the base sheet but also a form in which absorbent polymer pieces in, for example, particulate form are embedded and held in the base sheet, for example. Here, the form in which absorbent polymer pieces are embedded and held in the base sheet refers to a state where absorbent polymer pieces enter gaps between fibers of the base sheet, and extreme movement and detachment of absorbent polymer pieces do not easily occur even upon application of an external force to the base sheet. In this state, absorbent polymer pieces are attached to constituent fibers by tackiness of themselves, or constituent fibers are entangled or caught by absorbent polymer pieces. From the viewpoint of ensuring an absorbent polymer fixing proportion of 40% or more, however, the form in which absorbent polymer pieces are fixed to a surface of the base sheet with an adhesive interposed therebetween is more preferable than the form in which absorbent polymer pieces are embedded and held in the base sheet.

The adhesive 13 that is a base sheet fixing adhesive of the absorbent polymer 12 in the absorbent sheet 10 preferably has flexibility with which the adhesive 13 can extend in accordance with swelling variation caused by liquid absorption of the absorbent polymer 12, and is specifically preferably an acrylic, silicone-based, rubber-based, or olefin-based adhesive. For measurement of flexibility of the adhesive, a maximum ductility (elongation at breakage) of an adhesive measured according to Japan Adhesive Industry Association standard JAI7-1999 can be used as an index. It can be evaluated that as the maximum ductility increases, flexibility of the adhesive increases. The maximum ductility of the adhesive 13 is preferably 200% or more, and more preferably 300% or more. The maximum ductility, that is, flexibility, of the adhesive 13 is preferably as high as possible, and the upper limit of the maximum ductility is preferably 3000% or less, and more preferably 2500% or less.

Examples of materials (base polymer) for the acrylic adhesive include a (co)polymer (e.g., ethylene-vinyl acetate copolymer) of vinyl monomer including, as a main component, 2-ethylhexyl acrylate, butylacrylate, ethylacrylate, cyanoacrylate, vinyl acetate, and methyl methacrylate.

Examples of materials for the silicone-based adhesive (base polymer) include polydimethylsiloxane polymer.

Examples of materials (base polymer) for the rubber-based adhesive include natural rubber, polyisoprene, styrene-butadiene copolymer (SBR), styrene-isoprene-styrene block copolymer (SIS), styrene-butadiene-styrene block copolymer (SBS), styrene-ethylene-butadiene-styrene block copolymer (SEBS), and styrene-ethylene-propylene-styrene block copolymer (SEPS).

From the viewpoint of, for example, processability, the adhesive 13 is preferably a hot-melt adhesive that is used by heating and melting. The hot-melt adhesive typically contains base polymer, a tackifier, and a plasticizer. Specific examples of the base polymer are described above. In a case where the adhesive 13 is a hot-melt adhesive using SBS as base polymer, for example, a polystyrene block (hard segment) in the base polymer mainly contributes to appearance of a cohesive force of the adhesive, and a polybutadiene block (soft segment) in the base polymer contributes to appearance of rubber elasticity of the adhesive. Thus, to obtain the absorbent polymer fixing proportion of 40% or more as described above, a method of increasing the proportion of styrene in SBS is effective.

The tackifier constituting the hot-melt adhesive (adhesive 13) is preferably a tackifier that is solid at room temperature, and may be, for example, a C5-based petroleum resin, a C9-based petroleum resin, a dicyclopentadiene-based petroleum resin, a rosin-based petroleum resin, a polyterpene resin, or a terpene phenol resin. One of these resins may be used alone, or two or more of them may be used in combination.

The plasticizer constituting the hot-melt adhesive (adhesive 13) may be a paraffin-based oil or a naphthene-based oil. One of these oils may be used alone, or two or more of them may be used in combination.

The hot-melt adhesive (adhesive 13) may contain other components except the base polymer, the tackifier, and the plasticizer when necessary. Examples of the other components include phenol-based, amine-based, phosphorus-based, benzimidazole-based antioxidants. One of these antioxidants may be used alone, or two or more of them may be used in combination.

When the total amount of the tackifier and the plasticizer contained in the hot-melt adhesive is 100 parts by weight, the content of the base polymer in the hot-melt adhesive (adhesive 13) is preferably 10 parts by mass or more and more preferably 20 parts by mass or more, and is preferably 60 parts by mass or less and more preferably 40 parts by mass or less.

With respect to the total mass of the hot-melt adhesive, the content of the tackifier in the hot-melt adhesive (adhesive 13) is preferably 20 mass % or more, and more preferably 40 mass % or more, and preferably 80 mass % or less, and more preferably 70 mass % or less.

With respect to the total mass of the hot-melt adhesive, the content of the plasticizer in the hot-melt adhesive (adhesive 13) is preferably 0 mass % or more, and more preferably 10 mass % or more, and preferably 40 mass % or less, and more preferably 25 mass % or less.

The adhesive 13 for fixing the absorbent polymer 12 to the base sheet 11 needs to maintain fixing to the base sheet 11 after liquid absorption and swelling of the absorbent polymer 12 in order to obtain the absorbent polymer fixing proportion of 40% or more described above. Inventors of the present invention have conducted various studies on an adhesive that can satisfy the requirement, to find that such an adhesive needs to be extensible following swelling of absorbent polymer and to have resistance (residual stress) that prevents detachment of the absorbent polymer from the base sheet even upon application of an external force caused by swelling of the absorbent polymer. Through further study on the adhesive, the inventors also found that in a specific range of a residual stress upon application of an external force to the adhesive, the absorbent polymer fixing proportion of 40% or more can be obtained as intended. Based on the foregoing findings, a residual stress of the base sheet fixing adhesive as the adhesive 13 measured by the following method is preferably 3 kPa or more, and more preferably 5 kPa or more, and preferably 18 kPa or less, and more preferably 15 kPa or less.

Method for Measuring Residual Stress of Adhesive

With a rotary rheometer (manufactured by Anton Paar GmbH; Type: "Physica MCR301"), an adhesive as a measurement target is placed between a receiving plate supporting a measurement sample from below and having a circular shape in plan view and a pushing plate disposed above and opposed to the receiving plate and having a circular shape in plan view. The adhesive in this state has a circular shape in plan view, has a thickness of 1.5 mm and a diameter of 12 mm, and is at a temperature of 30° C. From this state, the pushing plate is rotated so that 30% of distortion is applied to the adhesive. After a lapse of 20 minutes from the application of distortion to the adhesive, a shearing stress of the adhesive is measured, and the obtained value is used as a residual stress of the adhesive.

In measuring the residual stress, in a case where the adhesive as a target of measurement is unused (a case where the adhesive is not applied to the base sheet and is not a constituent of the absorbent sheet), this unused adhesive is used as the target of measurement without change. On the other hand, in a case where the adhesive as a target of measurement is a constituent of the absorbent sheet, the adhesive is taken from the absorbent sheet by a solvent extraction method described below, and the obtained adhesive is used as a target of measurement. That is, the residual stress of the base sheet fixing adhesive as the adhesive 13 only needs to be in the preferred range described above in at least one of the unused state or the used state (i.e., state where the adhesive is applied to the base sheet 11).

Solvent Extraction Method of Adhesive

First, an absorbent sheet including an adhesive and a solvent in which the adhesive can be dissolved are mixed in a vessel such as a beaker, thereby obtaining an adhesive solution in which the adhesive is dissolved in the solvent. Next, the adhesive solution is taken from the vessel and is dried and hardened with a rotary evaporator under a reduced pressure, for example, so that the solvent is removed from the adhesive solution, thereby obtaining an adhesive. The thus-obtained adhesive is used as a measurement target in the measurement of the residual stress. The solvent for use in dissolving the adhesive is appropriately selected depending on, for example, the type of the adhesive. In a case where the adhesive as a measurement target is the adhesive (e.g., hot-melt adhesive) described above usable as the adhesive 13 (base sheet fixing adhesive), examples of the solvent for use in dissolving the adhesive include toluene, methyl ethyl ketone, and heptane.

For example, in a case where the base sheet fixing adhesive as the adhesive 13 is the hot-melt adhesive, the residual stress of the hot-melt adhesive can be adjusted by appropriately adjusting the composition of base polymer, the content of the plasticizer, and so forth.

In a case where the adhesive 13 is a hot-melt adhesive including SBS as base polymer, examples of a method for increasing the residual stress of the adhesive include a method of increasing the proportion of styrene constituting a cross-linked domain in SBS. The increase in styrene proportion strengthens the cross-linked domain and suppresses occurrence of stress relaxation caused by butadiene chains, resulting in an increase in residual stress of the adhesive. In contrast, in the case of reducing the residual stress of the hot-melt adhesive using SBS as base polymer, the proportion of styrene is reduced.

In the case where the base sheet fixing adhesive as the adhesive 13 is the hot-melt adhesive, a method for increasing the residual stress of the adhesive can be a method of reducing the proportion of the plasticizer such as paraffin oil. In contrast, in the case of reducing the residual stress of the hot-melt adhesive, the proportion of the plasticizer is reduced.

The absorbent sheet 10 can be produced by applying an adhesive (preferably a hot-melt adhesive) 13 to the first surface 11a of the base sheet 11, and then spraying absorbent polymer 12 (absorbent polymer pieces) onto the first surface 11a to which the adhesive is applied. The adhesive 13 is not limited to a specific pattern of application, and may be applied to the entire first surface 11a of the base sheet 11 or may be partially applied. In a case where the absorbent sheet 10 is used as an absorbent member of an absorbent product, for example, from the viewpoint of minimizing degradation of absorption performance by the adhesive 13, the adhesive 13 is preferably partially applied, that is, is preferably applied such that the first surface 11a of the base sheet 11 has both a portion to which the adhesive 13 is applied and a portion to which the adhesive 13 is not applied. The application of the adhesive 13 is not limited to a specific method, and known application methods, such as a slot spray method, a curtain spray method, a spiral spray method, a coater spray method, an omega spray method, and a summit spray method, may be employed. The application amount of the adhesive 13 in terms of solid content is preferably 1 $g/m^2$ or more, and more preferably 5 $g/m^2$ or more, and preferably 30 $g/m^2$ or less, and more preferably 20 $g/m^2$ or less.

The thickness and basis weight of the base sheet 11 and the basis weight (attachment amount per a unit area) of the absorbent polymer 12 are not limited to specific values, and appropriate values are selected depending on specific use of the absorbent sheet 10. In a case where the absorbent sheet 10 is used as an absorbent member of an absorbent product, for example, the absorbent sheet 10 is thin as a feature although the absorbent polymer 12 has a relatively large basis weight. Specifically, in the case where the absorbent sheet 10 is used as an absorbent member of an absorbent product, from the viewpoint of obtaining a thin and flexible absorbent member with a sufficient absorption capacity, the basis weight of the absorbent polymer 12 is preferably 30 $g/m^2$ or more, and more preferably 100 $g/m^2$ or more, and preferably 600 $g/m^2$ or less, and more preferably 400 $g/m^2$ or less.

From a similar viewpoint, the thickness (substantial thickness) of the base sheet 11 is preferably 0.01 mm or more, and more preferably 0.03 mm or more, and preferably 0.8 mm or less, and more preferably 0.2 mm or less. Unless otherwise specified, the "thickness of the sheet" herein refers to a thickness (thickness under a load of 0.5 $cN/cm^2$ (=0.05 kPa)) measured by a method described below.

From a similar viewpoint, the basis weight of the base sheet 11 is preferably 5 $g/m^2$ or more, and more preferably 8 $g/m^2$ or more, and preferably 40 $g/m^2$ or less, and more preferably 25 $g/m^2$ or less.

Method for Measuring Sheet Thickness

A circular plate having a weight of 2.5 g and a radius of 12.5 mm is placed on a measurement base, and the position of the upper surface of the circular plate in this state is defined as a reference point A for measurement. Next, the circular plate is removed, and a measurement target is placed on the measurement base, and the circular plate is placed again on the measurement target. The position of the upper surface of the circular plate in this state is defined as a position B. The measurement equipment is a displacement meter (manufactured by KEYENCE CORPORATION, CCD laser displacement sensor LK-080). A difference between the reference point A and the position B is defined as a thickness of the measurement target, that is, a thickness of the absorbent member under a pressure of 0.5 $cN/cm^2$ (=0.05 kPa).

In a case where a sheet (base sheet) of the measurement target is incorporated in an absorbent product, the sheet as a measurement target is removed from the absorbent product in the following manner. A cold spray (product name, manufactured by Nichiban Co., Ltd.) is applied to the topsheet of the absorbent product. Thereafter, constituents of the absorbent product except the measurement target are carefully detached from the absorbent product.

The absorbent sheet 10 can be used alone for absorption of liquid. For example, the absorbent sheet 10 may be used as a drip sheet, a sheet placed under food, and a sheet for pets. The absorbent sheet 10 may be also used as an absorbent member for use in various sanitary products such as a medical pad and a breast milk sheet. The absorbent sheet 10 is especially preferably used as an absorbent member in an absorbent product such as a sanitary napkin and a disposable diaper. The absorbent product typically includes a topsheet located close to the skin of a user and a backsheet located away from the skin of the user, and the absorbent sheet 10 is interposed between these sheets. The absorbent product including the absorbent sheet 10 shows high fixing performance of the absorbent polymer 12 to the base sheet 11, and even after liquid absorption, the absorbent polymer 12 is less likely to be detached from the base sheet 11. Thus, this absorbent product is less likely to suffer drawbacks due to the detachment of the absorbent polymer 12, such as fit degradation of the absorbent product caused by providing the absorbent product user with feeling of hardness or gritty feeling due to rubbing among the detached absorbent polymer 12, or liquid leakage and liquid return due to degradation of absorption performance.

FIG. 3 illustrates an absorbent member 20 that is one embodiment of an absorbent member according to the present invention. The embodiment of the present invention described later is mainly directed to components different from the absorbent sheet 10 described above, and components similar to those of the above embodiment are denoted by the same reference characters, and will not be repeated again. Description for the absorbent sheet 10 will be applied as appropriate to components not particularly described.

Figure 3A:
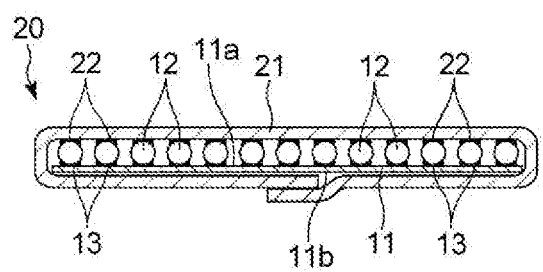
FIG. 3(a) is a cross-sectional view schematically illustrating a cross section along the thickness direction in a state before liquid absorption in one embodiment of the absorbent member according to the present invention.

As illustrated in FIG. 3(a), the absorbent member 20 includes the absorbent sheet 10 and a cover sheet 21 covering at least a surface of the absorbent sheet 10. The absorbent sheet 10 is disposed on an absorbent product such that the longitudinal direction X of the absorbent sheet 10 coincides with the longitudinal direction of the absorbent product corresponding to the front-rear direction of the absorbent product user, and the width direction Y of the absorbent sheet 10 coincides with the lateral direction orthogonal to the longitudinal direction. The cover sheet 21 serves as a sheet for receiving the absorbent sheet 10 during production of the absorbent member 20, and after the production, the cover sheet 21 wraps and shapes the absorbent sheet 10, for example. As described above, although the absorbent polymer 12 is hardly detached from the absorbent sheet 10, in case of detachment of the absorbent polymer 12, the cover sheet 21 is configured to prevent the detached absorbent polymer 12 from leaking out of the absorbent member 20.

In the absorbent sheet 10, the first surface 11a of the base sheet 11 that is the fixing surface of the absorbent polymer 12 is defined as a skin contact surface, and the second surface 11b is defined as a skin non-contact surface. Note that the "skin contact surface" herein refers to a surface of the absorbent product or a component thereof (e.g., the absorbent sheet 10) facing the skin of the user while the user puts on the absorbent product, that is, a side relatively close to the skin of the user, and the "skin non-contact surface" refers to a surface of the absorbent product or a component thereof opposite to the skin (side close to the clothing) while the user puts on the absorbent product, that is, a side relatively away from the user. The expression "while the user puts on the absorbent product" refers to a state where a normal appropriate put-on position is maintained.

The cover sheet 21 covers the skin contact surface and the skin non-contact surface of the absorbent sheet 10. In the absorbent member 20, as illustrated in FIG. 3(a), the cover sheet 21 is configured to include a skin side portion covering the skin contact surface (a side to which the absorbent polymer 12 is fixed) of the absorbent sheet 10 and a non-skin side portion covering the skin non-contact surface of the absorbent sheet 10. The skin side portion and the non-skin side portion constitute a single continuous sheet. More specifically, the absorbent member 20 employs the single continuous cover sheet 21 having a width twice or more and three times or less as large as the length of the absorbent sheet 10 in the width direction Y. As illustrated in FIG. 3(a), the single cover sheet 21 covers the entire skin contact surface of the absorbent sheet 10 and extends outward in the lateral direction Y from both ends of the absorbent sheet 10 in the lateral direction Y, and these extension portions are curled downward of the absorbent sheet 10 to cover the entire skin non-contact surface of the absorbent sheet 10. In the single cover sheet 21, a portion covering the skin contact surface of the absorbent sheet 10 is the skin side portion, and a portion covering the skin non-contact surface of the absorbent sheet 10 is the non-skin side portion. The cover sheet 21 can be a sheet member having water permeability, and may be, for example, paper and nonwoven fabrics. The basis weight of the cover sheet 21 is preferably 8 g/m$^2$ or more, and more preferably 12 g/m$^2$ or more, and preferably 30 g/m$^2$ or less, and more preferably 20 g/m$^2$ or less.

In the absorbent member 20, as illustrated in FIG. 3(a), the absorbent polymer 12 in the absorbent sheet 10 is fixed to the cover sheet 21 with a cover sheet fixing adhesive 22 interposed therebetween. That is, the absorbent polymer 12 is fixed to the first surface 11a of the base sheet 11 (skin contact surface) with interposition of the base sheet fixing adhesive 13 applied to the first surface 11a, and is fixed to the skin non-contact surface (surface facing the base sheet 11) of the skin side portion of the cover sheet 21 with interposition of the cover sheet fixing adhesive 22 applied to the skin non-contact surface. The absorbent polymer 12 is fixed to the cover sheet 21 between the opposed sheets 11 and 21 with interposition of the adhesives 13 and 22. The second surface 11b (skin non-contact surface) of the base sheet 11 is fixed to the skin contact surface of the non-skin side portion of the cover sheet 21 with the same adhesive (not shown) as the adhesive 22 interposed therebetween.

Figure 3B:
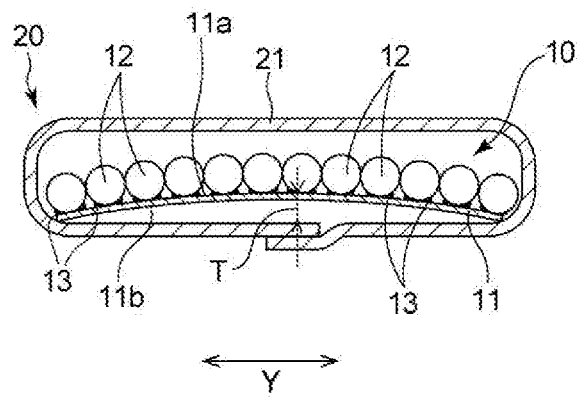
FIG. 3(b) is the same cross-sectional view in a state after liquid absorption of the absorbent member illustrated in FIG. 3(a).

FIG. 3(b) illustrates a state of the absorbent member 20 after liquid absorption. As illustrated in FIG. 3(b), in the state where the absorbent polymer 12 swells by liquid absorption in the absorbent sheet 10, the degree of bending of the base sheet 11 in the absorbent sheet 10 is larger than that before swelling of the absorbent polymer 12. Consequently, an apparent thickness T of the base sheet 11 (projecting height of a portion of the base sheet 11 projecting toward a skin contact surface 11a) is larger than that before swelling of the absorbent polymer 12. The bending of the base sheet 11 after liquid absorption and swelling of the absorbent polymer 12 and its accompanying increase in the apparent thickness T are due to the absorbent polymer fixing proportion of 40% or more obtained in the absorbent sheet 10. That is, in the absorbent sheet 10 having an absorbent polymer fixing proportion of 40% or more, even after the absorbent polymer 12 absorbs body fluid such as urine or menstrual blood and swells, a large part of the absorbent polymer 12 is still fixed to the first surface 11a of the base sheet 11. Thus, there is a relatively small room where the fixed absorbent polymer 12 swells so that the first surface 11a of the base sheet 11 is extended in the surface direction with swelling of the fixed absorbent polymer 12, whereas the second surface 11b of the base sheet 11, to which the absorbent polymer 12 is not fixed, is not extended in the surface direction. This difference in the degree of extension between the surfaces 11a and 11b of the base sheet 11 causes the base sheet 11 to bend and project toward the first surface 11a, that is, the skin side of the user. On the other hand, in a typical absorbent sheet not having an absorbent polymer fixing proportion of 40% or more, the proportion of absorbent polymer constituting the absorbent sheet detached due to liquid absorption and swelling is not small. Thus, even when absorbent polymer not detached and still fixed to the base sheet swells, the base sheet is not significantly extended in the surface direction, and as illustrated in FIG. 3(b), bending of the base sheet and an increase in apparent thickness less likely to occur.

In the state where the absorbent polymer 12 swells by liquid absorption, as illustrated in FIG. 3(b), the base sheet 11 bends and projects toward the skin contact surface and the apparent thickness T of the base sheet 11 becomes larger than that before swelling of the absorbent polymer 12. Accordingly, a gap is formed between the second surface 11b (skin non-contact surface) of the base sheet 11 and the cover sheet 21. This formation of the gap can enhance absorption of body fluid such as urine and menstrual blood so that liquid absorption performance of the absorbent member 20 can be enhanced.

In addition, the absorbent member 20 is configured such that adhesiveness of the adhesive 22 that fixes the absorbent polymer 12 to the cover sheet 21 is lower in the state where the absorbent polymer 12 swells by liquid absorption than that before swelling of the absorbent polymer 12. Thus, in this state, as illustrated in FIG. 3(b), fixing of the absorbent polymer 12 to the cover sheet 21 is canceled. Consequently, a gap can also be formed between the absorbent polymer 12 and the cover sheet 21 (the skin side portion) depending on the material and the basis weight, and so forth of the cover sheet 21 or the material, the basis weight, and so forth of an unillustrated topsheet closer to the skin of the user than the cover sheet 21. In a manner similar to the gap that can be formed at the non-skin side, such a gap that can be formed to the skin side of the base sheet 11 is also effective for enhancing absorption of body fluid such as urine and menstrual blood, and enhancement of liquid absorption performance of the absorbent member 20 can be expected.

In the manner described above, the base sheet fixing adhesive 13 and the cover sheet fixing adhesive 22 have different adhesivenesses in a wet state, and in the wet state, the adhesiveness of the base sheet fixing adhesive 13 is greater than that of the cover sheet fixing adhesive 22. The adhesive 22 may be a hot-melt adhesive typically used in this kind of absorbent member for bonding the absorbent core as the absorbent sheet and a cover sheet covering the absorbent core. The adhesive 22 has a residual stress measured by the method smaller than that of the adhesive 13. A preferred residual stress of the adhesive 13 is 3 kPa or more and 18 kPa or less as described above, whereas the residual stress of the adhesive 22 is typically less than 3 kPa.

In the "state where the apparent thickness T of the base sheet 11 is larger than that before swelling of the absorbent polymer 12 in the absorbent sheet 10" described above, that is, the state where the base sheet 11 is bent after swelling of the absorbent polymer 12, the state of the bending include not only a state where the entire base sheet 11 is bent but also a state where the base sheet 11 is partially bent, as illustrated in FIG. 3(b). Specifically, in a possible state, a plurality of bent portions in each of which a part of the base sheet 11 is bent and projects toward the skin contact surface are dispersed on the first surface 11a of the base sheet 11 after liquid absorption and swelling of the absorbent polymer 12. This difference in bent state of the base sheet 11 depends on the basis weight and arrangement pattern of the absorbent polymer 12, the type of base sheet 11, and so forth. Even in the state where the base sheet 11 has such partially bent portions, a gap can be formed between the absorbent sheet 10 and its opposed member as described above, and thus, advantages described above can be obtained.

As illustrated in FIG. 3(b), from the viewpoint of further ensuring deformation (bending) after liquid absorption of the absorbent sheet 10, the base sheet 11 is preferably flexible, specifically, has a flexural rigidity of preferably 10 cN or less, more preferably 5 cN or less, and even more preferably 3 cN or less. The flexural rigidity is measured by the following method.

Method for Measuring Flexural Rigidity

To measure a flexural rigidity, a handle-O-meter tester HOM-2 in conformity with JIS L1096 (Testing methods for woven fabrics: 2004) stiffness method E and manufactured by MFG. CO., LTD is used. A measurement sample having a square shape of 100 mm×50 mm in plan view is prepared, and is horizontally placed on a sample base of a tester whose slit interval is set at 30 mm such that a measurement portion of the measurement sample is located at the center between slits. At this time, the measurement sample is not fixed to the sample base. A blade adjusted to descend to a position of 8 mm (lowest position) from the surface of the sample base is moved downward at a constant speed of 200 mm/min from above the measurement sample. Then, a maximum value (cN) indicated by an indicator (load meter) obtained when the measurement sample is pushed by the blade forward and backward along the length is read. The measurement is performed three times on different measurement samples for each measurement target (base sheet) of the same type, and an average value is calculated and is used as a flexural rigidity of the measurement target. The measurement is performed at 23±2° C. and a humidity of 50±5%.

Although the present invention has been described based on the embodiment thereof, the present invention is not limited to this embodiment, and various modifications and changes may be made.

For example, in the embodiment, the absorbent polymer 12 is fixed only to the first surface 11a of the base sheet 11. Alternatively, the absorbing polymer 12 may be fixed only to the second surface 11b or to both the surfaces 11a and 11b. The configuration in which the absorbent polymer 12 is fixed to the both surfaces 11a and 11b of the base sheet 11 can hold a larger amount of absorbent polymer 12 than the configuration in which the absorbent polymer 12 is fixed to only one of the surface 11a or the surface 11b, and thus, the former configuration is preferable. Although the single continuous sheet is employed as the cover sheet 21 in the embodiment, alternatively, two sheets of a skin-side cover sheet covering the skin contact surface of the absorbent sheet 10 and a non-skin-side cover sheet covering a skin non-contact surface of the absorbent sheet 10 may be employed.

The absorbent product to which the absorbent sheet and the absorbent member according to the present invention generally include products for use in absorbing body fluid (e.g., urine, loose stool, menstrual blood, and sweat) emitted from a human body, and examples of such products include open type disposable diapers, pull-on disposable diapers, sanitary napkins, and a sanitary panties. Regarding the embodiment of the present invention described above, the following appendices are provided.

<1>

An absorbent sheet in which an absorbent polymer is fixed to a base sheet and an absorbent polymer fixing proportion measured in accordance with following processes 1 through 5 is 40% or more.

(Process 1) An absorbent sheet having 5 cm-square shape in plan view is prepared as a measurement sample. The measurement sample is temporarily suspended vertically with ends of the measurement sample being held, and then, the weight (initial sample weight) of the measurement sample is measured.

(Process 2) The entire measurement sample is immersed in physiological saline, and after 30 minutes from the start of immersion, the measurement sample is taken out of the physiological saline.

(Process 3) A cylindrical stirrer having a diameter of 35 mm and an axial length of 12 mm and 300 ml of physiological saline are placed in a beaker having a capacity of 300 ml, and the stirrer is rotated at the number of rotations of 600±5 rpm using a magnetic stirrer, thereby stirring the physiological saline. The measurement sample subjected to process 2 described above is placed in this physiological saline that is being stirred, and after 30 seconds from the placement, the measured sample is taken out of the physiological saline.

(Process 4) The measurement sample in a wet state subjected to process 3 is allowed to stand for 12 hours in a constant temperature bath whose internal temperature is set at 105° C., and the weight (post-stirring sample weight) of the measurement sample in a dried state is measured.

(Process 5) The total weight of members except absorbent polymer is subtracted from each of the initial sample weight and the post-stirring sample weight, thereby calculating an initial absorbent polymer weight (W0) and a post-stirring absorbent polymer weight (W1). Then, an absorbent polymer fixing proportion of the measurement sample (absorbent sheet) is calculated by:

$$\text{fixing percentage of absorbent polymer (\%)} = (W1/W0) \times 100$$

<2>

The absorbent sheet as set forth in clause <1> in which the absorbent polymer is fixed to the base sheet with a base sheet fixing adhesive interposed therebetween.

<3>

The absorbent sheet as set forth in clause <2> in which the base sheet fixing adhesive is an acrylic, silicone-based, or rubber-based adhesive.

<4>

The absorbent sheet as set forth in clause <2> or <3> in which the base sheet fixing adhesive is a hot-melt adhesive.

<5>

The absorbent sheet as set forth in any one of clauses <2> to <4> in which a maximum ductility of the base sheet fixing adhesive conforming to Japan Adhesive Industry Association standard JAI7-1999 is preferably 200% or more and more preferably 300% or more, and preferably 3000% or less and more preferably 2500% or less.

<6>

The absorbent sheet as set forth in any one of clauses <2> to <5> in which the base sheet fixing adhesive includes base polymer, a tackifier, and a plasticizer, and the base polymer is a styrene-butadiene-styrene block copolymer.

<7>

The absorbent sheet as set forth in clause <6> in which the tackifier is at least one selected from a group consisting of a C5-based petroleum resin, a C9-based petroleum resin, a dicyclopentadiene-based petroleum resin, a rosin-based petroleum resin, a polyterpene resin, and a terpene phenol resin.

<8>

The absorbent sheet as set forth in clause <6> or <7> in which the plasticizer is at least one selected from a group consisting of a paraffin-based oil and a naphthene-based oil.

<9>

The absorbent sheet as set forth in any one of clauses <6> to <8> in which when a total amount of the tackifier and the plasticizer included in the adhesive is 100 parts by weight, a content of the base polymer in the base sheet fixing adhesive is preferably 10 parts by mass or more and more preferably 20 parts by mass or more, and preferably 60 parts by mass or less and more preferably 40 parts by mass or less.

<10>

The absorbent sheet as set forth in any one of clauses <6> to <9> in which with respect to a total mass of the adhesive, a content of the tackifier in the base sheet fixing adhesive is preferably 20 mass % or more and more preferably 40 mass % or more, and preferably 80 mass % or less and more preferably 70 mass % or less.

<11>

The absorbent sheet as set forth in any one of clauses <6> to <10> in which with respect to a total mass of the adhesive, a content of the plasticizer in the base sheet fixing adhesive is preferably 0 mass % or more and more preferably 10 mass % or more, and preferably 40 mass % or less and more preferably 25 mass % or less.

<12>

The absorbent sheet as set forth in any one of clauses <2> to <11> in which a residual stress of the base sheet fixing adhesive is preferably 3 kPa or more and more preferably 5 kPa or more, and preferably 18 kPa or less and more preferably 15 kPa or less.

<13>

The absorbent sheet as set forth in any one of clauses <2> to <12> in which an amount of application of the base sheet fixing adhesive in terms of solid content is preferably 1 $g/m^2$ or more and more preferably 5 $g/m^2$ or more, and preferably 30 $g/m^2$ or less and more preferably 20 $g/m^2$ or less.

<14>

The absorbent sheet as set forth in any one of clauses <2> to <13> in which each surface of the base sheet is flat.

<15>

The absorbent sheet as set forth in clause <14> in which the absorbent polymer is fixed to a first surface of the base sheet with the base sheet fixing adhesive interposed therebetween, and the absorbent polymer is not fixed to a second surface of the base sheet.

<16>

The absorbent sheet as set forth in any one of clauses <1> to <14> in which the absorbent polymer is fixed to each surface of the base sheet.

<17>

The absorbent sheet as set forth in any one of clauses <1> to <16> in which a basis weight of the absorbent polymer is preferably 30 $g/m^2$ or more and more preferably 100 $g/m^2$ or more, and preferably 400 $g/m^2$ or less and more preferably 300 $g/m^2$ or less.

<18>

The absorbent sheet as set forth in any one of clauses <1> to <17> in which a centrifugal retentive capacity of the absorbent polymer is preferably 10 g/g or more, more preferably 20 g/g or more, and even more preferably 30 g/g or more, and preferably 60 g/g or less and more preferably 50 g/g or less.

<19>

The absorbent sheet as set forth in any one of clauses <1> to <18> in which the base sheet includes a nonwoven fabric or a resin film.

<20>

The absorbent sheet as set forth in any one of clauses <1> to <19> in which a flexural rigidity of the base sheet is preferably 10 cN or less, more preferably 5 cN or less, and even more preferably 3 cN or less.

<21>

The absorbent sheet as set forth in any one of clauses <1> to <20> in which a thickness of the base sheet is preferably 0.01 mm or more and more preferably 0.03 mm or more, and preferably 0.8 mm or less and more preferably 0.2 mm or less.

<22>

The absorbent sheet as set forth in any one of clauses <1> to <21> in which a basis weight of the base sheet is preferably 5 $g/m^2$ or more and more preferably 8 $g/m^2$ or more, and preferably 40 $g/m^2$ or less and more preferably 25 $g/m^2$ or less.

<23>

The absorbent sheet as set forth in any one of clauses <1> to <22> in which the base sheet is a nonwoven fabric.

<24>

The absorbent sheet as set forth in any one of clauses <1> to <23> in which the base sheet is a spunbond-meltblown-spunbond nonwoven fabric.

<25>

The absorbent sheet as set forth in any one of clauses <1> to <24> in which the absorbent polymer is particulate, and an average particle size of the absorbent polymer is preferably 50 µm or more and more preferably 200 µm or more, and preferably 800 µm or less and more preferably 500 µm or less.

<26>

An absorbent member including the absorbent sheet as set forth in any one of clauses <1> to <25> and a cover sheet covering at least a first surface of the absorbent sheet.

<27>

The absorbent member as set forth in clause <26> in which in a state where the absorbent polymer swells by liquid absorption in the absorbent sheet, an apparent thickness of the base sheet in the absorbent sheet is larger than that before swelling of the absorbent polymer.

<28>

The absorbent member as set forth in clause <27> in which the absorbent polymer is fixed to the cover sheet with a cover sheet fixing adhesive interposed therebetween, and in a state where the absorbent polymer swells by liquid absorption, an adhesiveness of the cover sheet fixing adhesive is lower than that before swelling of the absorbent polymer.

<29>

The absorbent member as set forth in clause <28> in which the absorbent polymer is fixed to the base sheet with a base sheet fixing adhesive interposed therebetween in the absorbent sheet, and the base sheet fixing adhesive and the cover sheet fixing adhesive have different adhesivenesses in a wet state, and the adhesiveness of the base sheet fixing adhesive is greater than that of the cover sheet fixing adhesive in the wet state.

<30>

The absorbent member as set forth in clause <28> or <29> in which the absorbent polymer is fixed to the base sheet with a base sheet fixing adhesive interposed therebetween, and the cover sheet fixing adhesive has a residual stress lower than that of the base sheet fixing adhesive.

<31>

The absorbent member as set forth in any one of clauses <26> to <30> in which a basis weight of the cover sheet is preferably 8 g/m² or more and more preferably 12 g/m² or more, and preferably 30 g/m² or less and more preferably 20 g/m² or less.

<32>

The absorbent member as set forth in any one of clauses <26> to <31> in which the cover sheet covers an entire region of a skin contact surface of the absorbent sheet and extends laterally outward from lateral ends of the absorbent sheet, and extension portions of the cover sheet are curled down toward a skin non-contact surface of the absorbent sheet to cover an entire region of the skin non-contact surface.

<33>

The absorbent member as set forth in any one of clauses <26> to <32> in which the absorbent polymer fixing proportion is 60% or more and more preferably 80% or more.

<34>

A method for producing the absorbent sheet as set forth in any one of clauses <1> to <25> including a step of applying an adhesive to a first surface of a base sheet and then spraying small pieces of absorbent polymer onto the first surface.

<35>

The method for producing the absorbent sheet as set forth in clause <34> in which a residual stress of the adhesive is 3 kPa or more and 18 kPa or less.

EXAMPLES

Examples of the present invention will now be specifically described, but the invention is not limited to the examples below.

Examples 1 Through 6 and Comparative Examples 1 and 2

An absorbent sheet having a configuration similar to that of the absorbent sheet 10 illustrated in FIGS. 1 and 2 were produced. As a base sheet, SMS nonwoven fabric having a basis weight of 10 g/m² was used in Examples 1 through 5 and Comparative Examples 1 and 2, and a PET film having a basis weight of 35 g/m² was used in Example 6. As an absorbent polymer, particulate polyacrylate-based absorbent polymer (average particle size: 400 µm, centrifugal retentive capacity: 27 g/g) was used. As a base sheet fixing adhesive for fixing absorbent polymer to a base sheet, a rubber-based hot-melt adhesive was used in Examples 1, 2, and 6 and Comparative Examples 1 and 2, an ethylene-vinyl acetate copolymer-based hot-melt adhesive was used in Example 3, a silicone-based adhesive was used in Example 4, and an acrylic adhesive was used in Example 5, and the basis weight of each adhesive in terms of solid content was 20 g/m².

Evaluation Test 1

For the absorbent sheets of Examples and Comparative Examples, an absorbent polymer fixing proportion was measured in accordance with processes 1 through 5. Table 1 shows results together with residual stresses of the base sheet fixing adhesives used in the examples and the comparative examples measured by the method.

Disposable diapers were also produced using the absorbent sheets of the examples and comparative examples. Specifically, an absorbent core (e.g., pulp fibers and an absorbent polymer as contents covered with a cover sheet) was removed from a disposable diaper (product name: "Merries", released on 2016) manufactured by Kao Corporation, and absorbent sheets of the examples and the comparative examples in the same shape and same dimensions as the removed absorbent core were wrapped by a cover sheet in a manner similar to the absorbent core and incorporated in the diaper. For the thus-produced disposable diaper, absorbent polymer fixing performance while a user puts on an absorbent product was evaluated by the following method. Table 1 below shows results.

Method for Evaluating Absorbent Polymer Fixing Performance while Putting on the Absorbent Product A diaper as an evaluation test is folded into two in the longitudinal direction with the skin contact surface, that is, the topsheet, turned inside, and both sides of a center portion of an absorbent member that is an injection target portion of an artificial urine are held by fingers so that the absorbent member is alternately moved in the vertical direction. This vertical movement is repeated 50 times, and then, each part of the diaper is extended so that the diaper is expanded in plane. Thereafter, with the topsheet facing upward and fixed on a horizontal plane, 120 g of artificial urine is injected into the topsheet in the center portion of the absorbent member, and the diaper is left for three minutes in a natural state.

Subsequently, the vertical movement performed before injection of the artificial urine is performed on the diaper again. This vertical movement is performed on the assumption of movement of legs of a user putting on a diaper. After 20 repetitions of the vertical movement, the cover sheet of the diaper is cut out, and the state of the absorbent sheet is visually observed. A case where detachment and/or movement of absorbent polymer is not observed at all or is only partially observed is defined as A (top rating), and the other case is defined as B.

A composition of artificial urine used in the measurement method is as follows: Urea: 1.94 mass %, sodium chloride: 0.7954 mass %, magnesium sulfate (heptahydrate): 0.11058 mass %, calcium chloride (dihydrate): 0.06208 mass %, potassium sulfate: 0.19788 mass %, polyoxyethylene lauryl ether: 0.0035 mass %, and ion-exchanged water (balance)

proportion is under 40% shows low absorbent polymer fixing performance during putting-on of an absorbent product, and in the evaluation test on the absorbent polymer fixing performance, the absorbent polymer significantly is detached and moved and large unevenness formed in the absorbent member is observed. From the foregoing results, the examples clearly is less likely to provide strange feeling during putting-on of an absorbent product due to detachment of an absorbent polymer as compared to the comparative examples, and can stably obtain high absorption performance.

Examples 7 Through 10

An absorbent sheet having a configuration similar to that of the absorbent sheet 10 illustrated in FIGS. 1 and 2 were produced. The nonwoven fabric or the resin film shown in Table 2 was used as a base sheet, and particulate polyacrylate-based absorbent polymer (average particle size: 400 µm) was used as absorbent polymer. A rubber-based hot-melt adhesive was used as a base sheet fixing adhesive for fixing the absorbent polymer to the base sheet, and the basis weight of the adhesive was 20 g/m² in terms of solid content.

TABLE 1

| | | Base sheet | | | Base sheet fixing adhesive | | | Absorbent polymer | Performance evaluation | |
|---|---|---|---|---|---|---|---|---|---|---|
| | | Type | Basis weight (g/m²) | Flexural rigidity (cN) | Type | Residual stress (kPa) | Basis weight (g/m²) | fixing proportion (%) | Absorbent polymer fixing property | in use of absorbent product |
| Example | 1 | SMS nonwoven fabric | 10 | 2.6 | rubber-based hot-melt adhesive | 3.6 | 20 | 61.7 | A | |
| | 2 | SMS nonwoven fabric | 10 | 2.6 | rubber-based hot-melt adhesive | 12.4 | 20 | 79.2 | A | |
| | 3 | SMS nonwoven fabric | 10 | 2.6 | ethylene-vinyl acetate copolymer-based hot-melt adhesive | 16.8 | 20 | 47.2 | A | |
| | 4 | SMS nonwoven fabric | 10 | 2.6 | silicone-based adhesive | 24.2 | 20 | 55.1 | A | |
| | 5 | SMS nonwoven fabric | 10 | 2.6 | acrylic adhesive | 7.5 | 20 | 64.2 | A | |
| | 6 | PET film | 35 | 2.8 | rubber-based hot-melt adhesive | 13.4 | 20 | 88.4 | A | |
| Comparative Example | 1 | SMS nonwoven fabric | 10 | 2.6 | rubber-based hot-melt adhesive | 2.2 | 20 | 10.7 | B | |
| | 2 | SMS nonwoven fabric | 10 | 2.6 | rubber-based hot-melt adhesive | 19.3 | 20 | 21.2 | B | |

As shown in Table 1, the absorbent sheet of each example having an absorbent polymer fixing proportion of 40% or more and the absorbent member using the absorbent sheet has high absorbent polymer fixing performance during putting-on of an absorbent product, and, even with movement after ejecting body fluid such as urine by a user, is less likely to cause detachment and movement of absorbent polymer and has a high shape retaining property. On the other hand, each comparative example whose absorbent polymer fixing Evaluation Test 2

Using the absorbent sheets of Examples 7 through 10, a disposable diaper was prepared in a manner similar to that described above. Thereafter, with the topsheet facing upward and fixed on a horizontal plane, 120 g of artificial urine was injected into the topsheet in the center portion of the absorbent member, and the diaper was left for three minutes in a natural state. Then, an apparent thickness of the base sheet after liquid adsorption (projecting height of a portion of the base sheet projecting toward the skin contact surface: a thickness indicated by character T in FIG. 3(b)) was measured. Table 2 shows results together with the substantial thickness of the base sheet previously measured before liquid absorption (before injection of artificial urine) in accordance with <Method for measuring sheet thickness>.

In any one of the absorbent sheets of Examples 7 through 10, the absorbent polymer fixing proportion measured in accordance with processes 1 through 5 was 40% or more.

TABLE 2

|  |  | Base sheet |  | Absorbent polymer | Performance evaluation | | |
|---|---|---|---|---|---|---|---|
|  |  |  |  |  | Substantial thickness | Apparent thickness of base sheet after | Thickness variation |
|  |  | Type | Basis weight (g/m²) | Flexural rigidity (cN) | Basis weight (g/m²) | of base sheet (mm) | liquid absorption (mm) | of base sheet (mm) |
| Example | 7 | Spunbond nonwoven fabric | 35 | 2.6 | 100 | 0.4 | 1.6 | 1.2 |
|  | 8 | PET film | 35 | 2.8 | 100 | 0.1 | 1.2 | 1.1 |
|  | 9 | Spunbond nonwoven fabric | 45 | 6.7 | 100 | 0.4 | 1.0 | 0.6 |
|  | 10 | PP film | 95 | 10.7 | 100 | 0.5 | 0.5 | 0.0 |

As described above, formation of a gap by bending of the base sheet after liquid absorption and swelling of the absorbent polymer can enhance a property of taking body fluid, and is favorable in terms of enhancement of absorption performance of the absorbent sheet. This gap corresponds to the "thickness variation of base sheet" (i.e., apparent thickness of base sheet after liquid adsorption—substantial thickness of base sheet) in Table 2. As the variation increases, the gap enlarges, and the property of taking body fluid increases in evaluation.

As shown in Table 2, since the difference in thickness variation of the base sheet is significant between the Examples 7 and 8 and Example 9, it is found that the flexural rigidity of the base sheet is preferably about 6 cN or less, especially about 3 cN or less.

INDUSTRIAL APPLICABILITY

The present invention provides an absorbent sheet and an absorbent member showing a high property of fixing absorbent polymer to a base sheet and less likely to suffer from detachment of absorbent polymer even after liquid absorption. Upon application of the absorbent sheet or the absorbent member according to the present invention to an absorbent product, detachment of the absorbent polymer is effectively suppressed. Thus, strangeness is less likely to be felt by a user, and absorption performance can be stably obtained.

The invention claimed is:

1. An absorbent member comprising:
an absorbent sheet comprising a base sheet and an absorbent polymer is fixed to the base sheet on a first skin-facing surface side of the absorbent sheet; and a cover sheet covering at least a portion of the first skin-facing surface side of the absorbent sheet, wherein the absorbent polymer is fixed to the cover sheet with a cover sheet fixing adhesive interposed therebetween, and in a state where the absorbent polymer swells by liquid absorption, an adhesiveness of the cover sheet fixing adhesive is lower than that before swelling of the absorbent polymer,
the absorbent polymer is fixed to the base sheet with a base sheet fixing adhesive interposed therebetween in the absorbent sheet, and the base sheet fixing adhesive and the cover sheet fixing adhesive have different adhesivenesses in a wet state, and the adhesiveness of the base sheet fixing adhesive is greater than that of the cover sheet fixing adhesive in the wet state, and
an absorbent polymer fixing proportion to the base sheet is 40% or more; and
wherein swelling by liquid absorption of the absorbent polymer fixed to the base sheet of the absorbent sheet causes at least a portion or an entirety of the base sheet to bend and project toward the first skin-facing surface side of the absorbent sheet, and thereby forming a gap between a second non-skin-facing surface side of the base sheet of the absorbent sheet and a portion of the cover sheet covering at least a portion of a second non-skin-facing surface side of the absorbent sheet; and
wherein swelling by liquid absorption of the absorbent polymer fixed to the base sheet of the absorbent sheet on the first skin-facing surface side of the absorbent sheet causes a gap to form between the base sheet of the absorbent sheet and the cover sheet covering at least the portion of the first skin-facing surface side of the absorbent sheet.

2. The absorbent member according to claim 1, wherein the base sheet fixing adhesive is an acrylic, silicone-based, or rubber-based adhesive.

3. The absorbent member according to claim 1, wherein the base sheet fixing adhesive is a hot-melt adhesive.

4. The absorbent member according to claim 1, wherein a residual stress of the base sheet fixing adhesive is 3 kPa or more and 18 kPa or less.

5. The absorbent member according to claim 1, wherein the base sheet includes a nonwoven fabric or a resin film.

6. The absorbent member according to claim 1, wherein a flexural rigidity of the base sheet is 10 cN or less.

7. The absorbent member according to claim 1, wherein in a state where the absorbent polymer swells by liquid absorption in the absorbent sheet, an apparent thickness of the base sheet in the absorbent sheet is larger than that before swelling of the absorbent polymer.

8. An absorbent article comprising:
the absorbent member according to claim 1.

9. The absorbent article according to claim 8, wherein the cover sheet fixing adhesive has a residual stress lower than that of the base sheet fixing adhesive.

10. The absorbent article according to claim 8, wherein the base sheet fixing adhesive is an acrylic, silicone-based, or rubber-based adhesive.

11. The absorbent article according to claim 10, wherein the base sheet fixing adhesive is a hot-melt adhesive.

12. The absorbent article according to claim 11, wherein a residual stress of the base sheet fixing adhesive is 3 kPa or more and 18 kPa or less.

13. The absorbent member according to claim 1, wherein a residual stress of the base sheet fixing adhesive is 3 kPa or more and 18 kPa or less, and
wherein a residual stress of the cover sheet fixing adhesive is less than 3 kPa.

\* \* \* \* \*